United States Patent
Takahashi et al.

(10) Patent No.: US 6,806,387 B2
(45) Date of Patent: Oct. 19, 2004

(54) PROCESS FOR PREPARATION OF ALLYL SULFONE DERIVATIVES AND INTERMEDIATES FOR THE PREPARATION

(75) Inventors: Toshiya Takahashi, Kawanishi (JP); Hirotada Kakiya, Ibaraki (JP); Shinzo Seko, Oita (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/250,306

(22) PCT Filed: Sep. 9, 2002

(86) PCT No.: PCT/JP02/09142

§ 371 (c)(1),
(2), (4) Date: Jun. 30, 2003

(87) PCT Pub. No.: WO03/022803

PCT Pub. Date: Mar. 20, 2003

(65) Prior Publication Data

US 2004/0054233 A1 Mar. 18, 2004

(30) Foreign Application Priority Data

Sep. 10, 2001 (JP) .................................. 2001-273202

(51) Int. Cl.⁷ ...................... C07C 315/00; C07C 317/00
(52) U.S. Cl. ............................................ 568/32; 568/28
(58) Field of Search ..................................... 568/28, 32

(56) References Cited

U.S. PATENT DOCUMENTS

| | | | | |
|---|---|---|---|---|
| 4,825,006 A | * | 4/1989 | Otera et al. ................ | 568/32 |
| 6,348,622 B1 | * | 2/2002 | Takahashi et al. .......... | 560/260 |
| 6,660,888 B2 | * | 12/2003 | Takahashi et al. ........... | 568/32 |

FOREIGN PATENT DOCUMENTS

| | | |
|---|---|---|
| EP | 1199 303 A1 | 4/2002 |
| EP | 1199303 A1 | 4/2002 |
| JP | WO 02/62752 A1 | 4/2002 |
| JP | 2002-193917 A | 7/2002 |
| JP | 2002-193918 A | 7/2002 |
| JP | 2002-193920 A | 7/2002 |
| WO | WO 00/24713 A1 | 5/2000 |

OTHER PUBLICATIONS

CA:132:293897 abs of WO 2000024713 May 2000.*
CA:139:53171 abs of JP2003171362 Jun. 2003.*
CA:139:230876 abs of Wo 2003070698 Aug. 2003.*

* cited by examiner

Primary Examiner—Jean F. Vollano
(74) Attorney, Agent, or Firm—Birch, Stewart, Kolasch & Birch, LLP

(57) ABSTRACT

The present invention relates to a process for producing an allyl sulfone derivative represented by the formula (3):

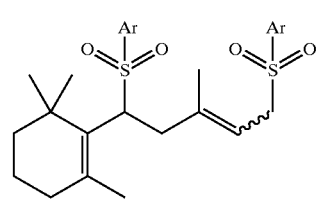

(3)

wherein Ar is an optionally substituted aryl group, and the corrugated line means either one of E/Z geometrical isomers, or a mixture thereof, which is an intermediate for producing vitamin A, which process is characterized by reacting an aryl sulfinic acid or a salt thereof represented by the formula (2):

$$ArSO_2M \quad (2)$$

wherein Ar is as defined above, and M is hydrogen atom, sodium atom or potassium atom, with an allyl halide derivative represented by the formula (1):

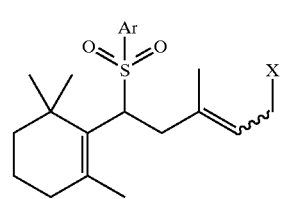

(1)

wherein X is a halogen atom, and Ar and the corrugated line are as defined above.

23 Claims, No Drawings

PROCESS FOR PREPARATION OF ALLYL SULFONE DERIVATIVES AND INTERMEDIATES FOR THE PREPARATION

This application is the national phase under 35 U.S.C. §371 of PCT International Application No. PCT/JP02/09142 which has an International filing date of Sep. 9, 2002, which designated the United States of America.

TECHNICAL FIELD

The present invention relates to a process for producing an allyl sulfone derivative which is a starting material for vitamin A derivatives and various terpene compounds to be used for medicament, feed additives, food additives, etc., and an intermediate for producing it.

BACKGROUND ART

As a process for producing a vitamin A derivative, there has been known a process using an intermediate compound obtained by reacting a halogen compound, which is derived from a C10 alcohol compound such as linalool, geraniol, or the like by a reaction step using an expensive Pd catalyst and a ligand, with a C10 sulfone (a compound represented by the formula (7) described below) to introduce a C10 side chain (EP 900785 A).

DISCLOSURE OF THE INVENTION

According to the process of the present invention, an allyl sulfone derivative represented by the formula (3) described below which is useful as an intermediate for producing vitamin A derivatives and the like, can be industrially and advantageously produced from a halide compound (a compound represented by the formula (8) described below) without requiring an expensive Pd catalyst and a ligand, thereby requiring no recovery step thereof.

That is, the present invention provides:

1. An allyl halide derivative represented by the formula (1):

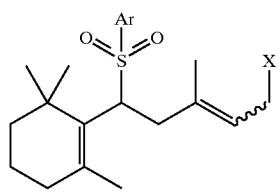

(1)

wherein Ar is an optionally substituted aryl group, X is a halogen atom, and the corrugated line means either one of E/Z geometrical isomers or a mixture thereof;

2. A process for producing an allyl sulfone derivative represented by the formula (3):

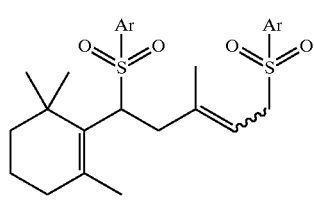

(3)

wherein Ar and the corrugated line are as defined above, which comprises reacting an aryl sulfinic acid or a salt thereof, represented by the formula (2):

$$ArSO_2M \quad (2)$$

wherein Ar is as defined above, and M is hydrogen atom, sodium atom or potassium atom, with an allyl halide derivative represented by the formula (1):

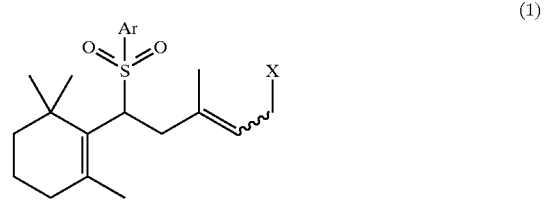

(1)

wherein Ar, X and the corrugated line are as defined above; and

3. A process for producing the above allyl halide represented by the formula (1) which comprises subjecting an allyl alcohol derivative represented by the formula (5):

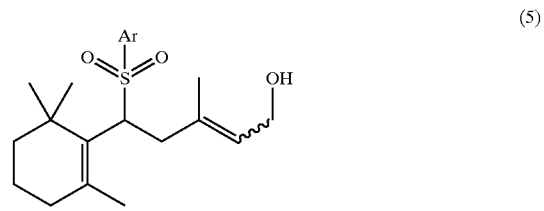

(5)

wherein Ar and the corrugated line are as defined above, to a halogenation reaction.

MODE FOR CARRYING OUT THE INVENTION

Detailed explanation of the present invention will be set forth hereinafter.

Ar of the compounds represented by respective formulas in the present invention is an optionally substituted aryl group. Examples of the aryl group include phenyl group, naphthyl group, and the like, and examples of the substituent thereof include a C1 to C5 straight or branched chain alkyl group (e.g., methyl, ethyl, propyl, isopropyl, butyl, pentyl, etc.), a C1 to C5 straight or branched chain alkoxy group (methoxy, ethoxy, propoxy, isopropoxy, butoxy, pentyloxy, etc.), a halogen atom (fluorine, chlorine, bromine, iodine), nitro group, and the like. Specifically, there are phenyl, naphthyl, o-tolyl, m-tolyl, p-tolyl, o-methoxyphenyl, m-methoxyphenyl, p-methoxyphenyl, o-chlorophenyl, m-chlorophenyl, p-chlorophenyl, o-bromophenyl, m-bromophenyl, p-bromophenyl, o-iodophenyl, m-iodophenyl, p-iodophenyl, o-fluorophenyl, m-fluorophenyl, p-fluorophenyl, o-nitrophenyl, m-nitrophenyl, p-nitrophenyl, and the like.

Further, the substituent X represents a halogen atom and, specifically, there are chlorine atom, bromine atom and iodine atom.

In the present invention, the allyl halide derivative (1) can be produced by reacting a halogenation agent with the allyl alcohol derivative of the above formula (5).

The halogenation agent is not specifically limited and, for example, reactive halides such as a group 4 transition metal halide, a sulfur, phosphorus or boron halide, an acid chloride, and the like can be exemplified. These halogenation agents can be reacted in the presence of a formamide compound. Of course, the halogenation reaction can be carried out in the presence of a Vilsmeyer complex formed by the above halogenation agent and a formamide compound.

As to respective halogenation agents, more detailed explanation will be set forth hereinafter.

Examples of the group 4 transition metal halide include titanium tetrachloride, titanium tetrabromide, titanium tetraiodide, dichlorotitanium diisopropoxide, chlorotitanium triisopropoxide, zirconium tetrachloride, zirconium tetrabromide, zirconium tetraiodide, hafnium tetrachloride, hafnium tetrabromide, hafnium tetraiodide, and the like. Usually, the amount thereof to be used is about 0.3 to 5 mole, preferably about 1 to 3 mole per 1 mole of the ally alcohol derivative (5). Usually, a solvent is used for this reaction. Examples of such solvent include ether solvents such as diethyl ether, tetrahydrofuran, 1,4-dioxane, dimethoxyethane, anisole, etc.; hydrocarbon solvents such as n-hexane, cyclohexane, n-pentane, benzene, toluene, xylene, etc.; halogenated hydrocarbon solvents such as chloroform, dichloromethane, 1,2-dichloroethane, monochlorobenzene, o-dichlorobenzene, etc.; ketone solvents such as acetone, methyl ethyl ketone., methyl isobutyl ketone, acetylacetone, etc.; or aprotic polar solvents such as acetonitrile, N,N-dimethylformamide, dimethyl sulfoxide, N,N-dimethylacetamide, hexamethylphosphoric triamide, etc. They may be used alone or in the form of a mixed solvent of two or more thereof.

Preferably, the above halogenation reaction is carried out, for example, in the presence a coordination compound such as an ether compound inclusive the above ether solvent or a ketone compound inclusive the above ketone solvent. They may be used alone or in the form of a mixture of two or more thereof.

Examples of the coordination compound include C2 to C10 straight or branched ether compounds and ketone compounds. Specifically, as the ether compounds, there are dimethyl ether, methyl ethyl ether, diethyl ether, methyl t-butyl ether, methyl cellosolve, ethylene glycol dimethyl ether, diethylene glycol dimethyl ether, triethylene glycol dimethyl ether, tetraethylene glycol dimethyl ether, tetrahydrofuran, 1,4-dioxane, and the like; and as the ketone compounds, there are acetone, diethyl ketone, methyl ethyl ketone, methyl isobutyl ketone, methyl t-butyl ketone, cyclopentenone, cyclohexanone, and the like.

The amount of the coordination compound to be used may be that sufficient to serve as a solvent regardless of a halogenation agent to be used and the addition of about 5 mole thereof per 1 mole of the allyl alcohol derivative (5) is sufficient. Usually, the reaction temperature can be freely selected within the range of −78° C. to the boiling point of a solvent but, preferably, within the range of about −20 to 80° C.

Examples of the sulfur, phosphorus or boron halide and the acid chloride include thionyl chloride, thionyl bromide, phosphorus trichloride, phosphorus pentachloride, phosphorus oxytrichloride, phosphorus tribromide, phosphorus pentabromide, phosphorus triiodie, boron trichloride, boron tribromide, boron triiodie, phosgene, oxalyl chloride, and the like. Usually, the amount thereof to be used is about 0.3 to 5 moles, preferably, about 1 to 3 moles per 1 mole of the allyl alcohol derivative (5).

Usually, a solvent is used for this reaction. Examples of such solvent include ether solvents such as diethyl ether, tetrahydrofuran, 1,4-dioxane, dimethoxyethane, anisole, etc.; hydrocarbon solvents such as n-hexane, cyclohexane, n-pentane, benzene, toluene, xylene, etc.; halogenated hydrocarbon solvents such as chloroform, dichloromethane, 1,2-dichloroethane, monochlorobenzene, o-dichlorobenzene, etc.; ketone solvents such as acetone, methyl ethyl ketone, methyl isobutyl ketone, acetylacetone, etc.; or aprotic polar solvents such as acetonitrile, N,N-dimethylformamide, dimethyl sulfoxide, N,N-dimethylacetamide, hexamethylphosphoric triamide, etc. The reaction temperature can be freely selected within the range of −78° C. to the boiling point of a solvent but, preferably, within the range of about −20 to 80° C.

A Vilsmeyer complex can be formed by coexisting a halogenation agent such as thionyl chloride, thionyl bromide, phosphorus trichloride, phosphorus pentachloride, phosphorus oxytrichloride, phosphorus tribromide, phosphorus pentabromide, phosphorus triiodie, boron trichloride, boron tribromide, boron triiodie, phosgene, oxalyl chloride, or the like with a formamide compound to carry out the halogenation reaction. As the formamide compound to be used together with these halogenation agents, there are N,N-dimethylformamide, N-methylformamide, formamide, N-methylformanilide, and the like. Usually, the amount of the halogenation agent to be used is about 0.3 to 5 moles, preferably about 0.5 to 3 moles per 1 mole of the allyl alcohol derivative (5). Further, usually, the amount of the formamide compound to be used is about 0.3 to 5 moles, preferably about 0.5 to 3 moles per 1 mole of the allyl alcohol derivative (5).

Usually, a solvent is used for this reaction. Examples of such solvent include ether solvents such as diethyl ether, tetrahydrofuran, 1,4-dioxane, dimethoxyethane, anisole, etc.; hydrocarbon solvents such as n-hexane, cyclohexane, n-pentane, benzene, toluene, xylene, etc.; halogenated hydrocarbon solvents such as chloroform, dichloromethane, 1,2-dichloroethane, monochlorobenzene, o-dichlorobenzene, etc.; ketone solvents such as acetone, methyl ethyl ketone, methyl isobutyl ketone, acetylacetone, etc.; and aprotic polar solvents such as acetonitrile, N,N-dimethylformamide, dimethyl sulfoxide, N,N-dimethylacetamide, hexamethylphosphoric triamide, etc. The reaction temperature can be freely selected within the range of −78° C. to the boiling point of a solvent but, preferably, within the range of about −20 to 50° C.

After the reaction, the allyl halide derivative (1) can be obtained by carrying out a conventional work up procedure. If necessary, it can be purified by extraction, washing, various kinds of chromatography, and the like.

The ally sulfinic acid represented by the formula (2) or a salt thereof can be obtained by reducing an aryl sulfonyl chloride represented by the formula (4):

$$ArSO_2Cl \qquad (4)$$

wherein Ar is an optionally substituted aryl group. Preferably, this reduction reaction is carried out in the presence of a reducing agent and a base in water. As the reducing agent, a sulfite or a bisulfite is preferred and, specifically, there are, for example, sodium sulfite, potassium sulfite, sodium bisulfite, potassium bisulfite and the like. Usually, the amount thereof to be used is within the range of about 1 to 2.5 moles, preferably about 1 to 2 moles per 1 mole of the aryl sulfonyl chloride (4). As the base to be present together with the reducing agent, preferred are an alkali metal hydroxide, an alkali metal carbonate, an alkali metal bicarbonate, and the like. Specifically, examples thereof include sodium hydroxide, potassium hydroxide, sodium carbonate, potassium carbonate, sodium bicarbonate, potassium bicarbonate, and the like. Usually, the amount thereof to be used is within the range of about 1 to 5 moles, preferably about 1 to 2.5 moles per 1 mole of the aryl sulfonyl chloride (4) and the reaction temperature is, usually, within the range of 0 to 100° C., preferably within the range of about 20 to 70° C.

After completion of the reaction, the aryl sulfinic acid or a salt thereof obtained can be isolated. Alternatively, the ally sulfone derivative (3) can be obtained from the aryl sulfonyl chloride by one-pot operation without isolation of thus-produced aryl sulfinic acid or a salt thereof by addition of the allyl halide derivative (1) to the reaction mixture. Usually, the amount of the ally halide derivative (1) to be added is within the range of about 0.3 to 1.2 moles, preferably about 0.7 to 1 moles per 1 mole of the aryl sulfonyl chloride (4).

It is preferable to carry out the above reaction in a biphasic system consisting of water and a hydrophobic organic solvent in the presence of a phase-transfer catalyst. Examples of the hydrophobic organic solvent to be used include hydrocarbon solvents such as n-hexane, n-heptane, cyclohexane, benzene, toluene, xylene, etc.; halogenated hydrocarbon solvents such as 1-chlorobutane, 1,2-dichloroethane, chlorobenzene, o-dichlorobenzene, trifluoromethylbenezene, etc.; ketone solvents such as acetone, methyl isobutyl ketone, etc.; ester solvents such as methyl acetate, ethyl acetate, etc.; amide solvents such as N,N-dimethylformamide, etc.; and ether solvents such as methyl t-butyl ether, etc.

Examples of the phase-transfer catalyst to be used include a quaternary ammonium salt, a quaternary phosphonium salt, a sulfonium salt, etc. As the quaternary ammonium salt, there are, for example, tetramethylammonium chloride, tetraethylammonium chloride, tetrapropylammonium chloride, tetrabutylammonium chloride, tetraoctylammonium chloride, tetrahexadecylammonium chloride, tetraoctadecylammonium chloride, benzyltrimethylammonium chloride, benzyltriethylammonium chloride, benzyltributylammonium chloride, 1-methylpyridinium chloride, 1-hexadecylpyridinium chloride, 1,4-dimethylpyridinium chloride, tetramethyl-2-butylammonium chloride, trimethylcyclopropylammonium chloride, tetramethylammonium bromide, tetraethylammonium bromide, tetrapropylammonium bromide, tetrabutylammonium bromide, tetraoctylammonium bromide, tetrahexadecylammonium bromide, tetraoctadecylammonium bromide, benzyltrimethylammonium bromide, benzyltriethylammonium bromide, benzyltributylammonium bromide, 1-methylpyridinium bromide, 1-hexadecylpyridinium bromide, 1,4-dimethylpyridinium bromide, trimethylcyclopropylammonium bromide, tetramethylammonium iodide, tetraethylammonium iodide, tetrabutylammonium iodide, tetraoctylammonium iodide, t-butylethyldimethylammonium iodide, tetradecyltrimethylammonium iodide, hexadecyltrimethylammonium iodide, octadecyaltrimethylammonium iodide, benzyltrimethylammonium iodide, benzyltriethylammonium iodide, benzyltributylammonium iodide, tetramethylammonium hydrogensulfate, tetraethylammonium hydrogensulfate, tetrabutylammonium hydrogensulfate, and the like.

As the quaternary phosphonium salt, there are, for example, tetraethylphosphonium chloride, triethylbenzylphosphonium chloride, tetrabutylphosphonium chloride, tributylmethylphosphonium chloride, tributyloctylphosphonium chloride, tributylhexadecylphosphonium chloride, tributylallylphosphonium chloride, tributylbenzylphosphonium chloride, trioctylethylphosphonium chloride, tetraphenylphosphonium chloride, tetraethylphosphonium bromide, triethylbenzylphosphonium bromide, tetrabutylphosphonium bromide, tributylmethylphosphonium bromide, tributyloctylphosphonium bromide, tributylhexadecylphosphonium bromide, tributylallylphosphonium bromide, tributylbenzylphosphonium bromide, trioctylethylphosphonium bromide, tetraphenylphosphonium bromide, tetraethylphosphoriium iodide, triethylbenzylphosphonium iodide, tetrabutylphosphonium iodide, tributylmethylphosphonium iodide, tributyloctylphosphonium iodide, tributylhexadecylphosphonium iodide, tributylallylphosphonium iodide, tributylbenzylphosphonium iodide, trioctylethylphosphonium iodide, tetraphenylphosphonium iodide, and the like.

As the sulfonium salt, there are, for example, dibutylmethylsuflonium chloride, trimetylsulfonium chloride, triethylsulfonium chloride, dibutylmethylsulfonium bromide, trimethylsulfonium bromide, triethylsulfonium bromide, dibutylmethylsulfonium iodide, trimethylsulfonium iodide, triethylsulfonium iodide, and the like.

Among these phase-transfer catalysts, iodides are preferred with a quaternary ammonium iodide being particularly preferred.

Usually, the amount of a phase-transfer catalyst to be used is within the range of about 0.001 to 0.2 mole, preferably about 0.01 to 0.1 mole per 1 mole of the allyl halide derivative (1).

Usually, the reaction temperature is within the range of 30 to 110° C., preferably about 50 to 100° C.

Further, addition of an inorganic salt is more preferred and examples thereof include alkali metal and alkaline earth metal halides. Specifically, sodium chloride, potassium chloride, sodium bromide, potassium bromide, calcium chloride, magnesium chloride, etc., are exemplified. The amount of such inorganic salt to be used varies depending on an amount of water as a solvent but, usually, it is within the range of about 50 to 1000% by weight, preferably about 100 to 300% by weight based on an amount of the allyl halide derivative (1).

After the reaction, the allyl sulfone derivative (3) obtained can be isolated and purified by extraction, washing, crystallization, various chromatography, and the like.

The starting compound, i.e., the ally alcohol derivative (5), can be simply and readily produced according to a method shown by the following scheme. That is, the allyl alcohol derivative (5) can be obtained by reacting the sulfone (7) and the halide (8) under basic conditions and deprotecting the protected hydroxy group of the resultant sulfone derivative (9) according to a conventional method (for example, in case of an acyl group such as R=acetyl group, etc., alkaline hydrolysis).

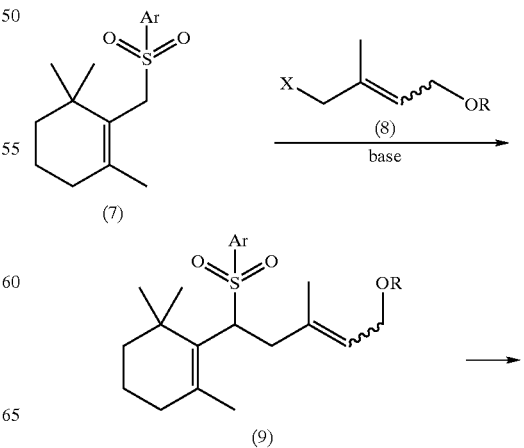

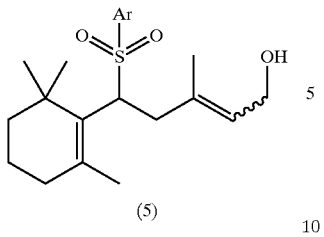

(5)

The sulfone (7) can be produced by a method described in Chem. Lett., 479 (1975). Further, the halide (8) can be simply and readily obtained from isoprene by two steps according to the method described in the specification of U.S. Pat. No. 4,175,294.

Furthermore, from the allyl sulfone derivative (3), retinol can be derived according to the following scheme. That is, retinol can be simply and readily obtained by reacting the allyl sulfone derivative (3) with the halide (8), and reacting the resultant disulfone derivative (10) with a base. The allyl sulfone derivative (3) is an important intermediate for retinol useful as medicament, feed additives and food additives.

Scheme

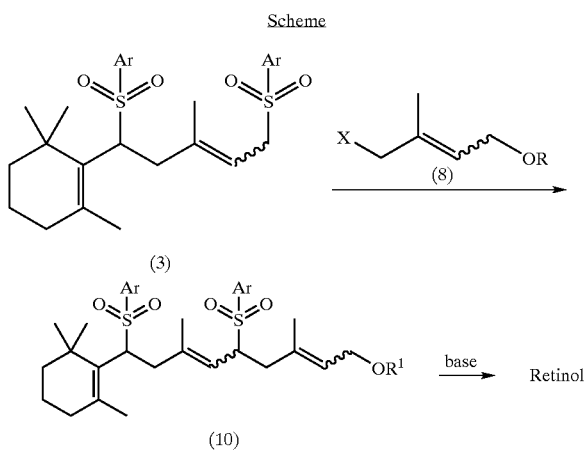

EXAMPLES

The following examples further illustrate the present invention in detail but the present invention are not limited by these examples.

Example 1

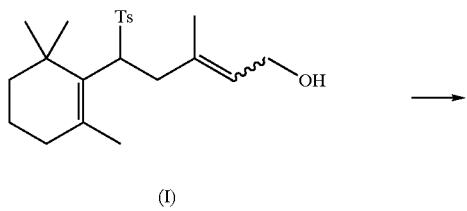

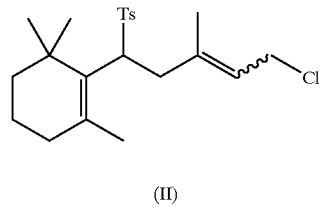

(II)

Alcohol (I) (1.0 g (2.68 mmole)) was dissolved in dimethoxyethane (hereinafter abbreviated as DME) (30 ml) at room temperature and 1 M TiCl$_4$ solution (9.5 ml) in toluene was added dropwise thereto at the same temperature. After addition, the temperature of the reaction mixture was raised to 60° C., followed by stirring for 30 hours. After completion of the reaction, the reaction mixture was poured into water and the mixture was extracted with ethyl acetate. The organic layer thus obtained was washed in sequence with an aqueous saturated sodium bicarbonate solution and saturated saline and dried over anhydrous magnesium sulfate, and the solvent was distilled off. The resultant yellow oily material was purified by silica gel chromatography to obtain allyl halide (II) in a yield of 55%.

Allyl Halide (II)

$^1$H-NMR (CDCl$_3$): δ 0.46 (3H, s), 0.69 (3H, s), 0.98 (3H, s), 1.01–1.26 (4H, m), 1.63 (3H, s), 1.63–1.84 (2H, m), 2.45 (3H, s), 2.26 (1H, d, J=6 Hz), 2.32 (1H, d, J=6 Hz), 3.52 (1H, d, J=7 Hz), 3.59 (1H, d, J=7 Hz), 5.09 (1H, t, J=7 Hz), 7.39 (2H, d, J=7 Hz), 7.42 (2H, d, J=7 Hz).

Example 2

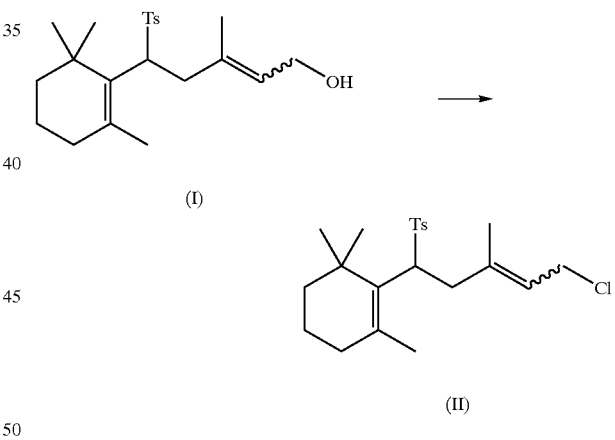

Alcohol (I) (trans/cis=96/4; 188 mg (0.5 mmole)) was dissolved in acetone (3.3 ml) at room temperature and 1 M TiCl$_4$ solution (1.2 ml) in toluene was added dropwise thereto at 0° C. After stirring at the same temperature for 2 hours, the temperature of the reaction mixture was raised to room temperature, followed by stirring at the same temperature for 6.5 hours. After completion of the reaction, the reaction mixture was poured into water, and the mixture was extracted with ethyl acetate. The resultant organic layer was washed in sequence with an aqueous saturated sodium bicarbonate solution and saturated saline and dried over anhydrous sodium sulfate, and the solvent was distilled off to obtain a yellow oily crude product. When the crude product thus obtained was quantified by high performance liquid chromatography (HPLC), the yield of allyl halide (II) was 97% (trans/cis=84/16).

Example 3

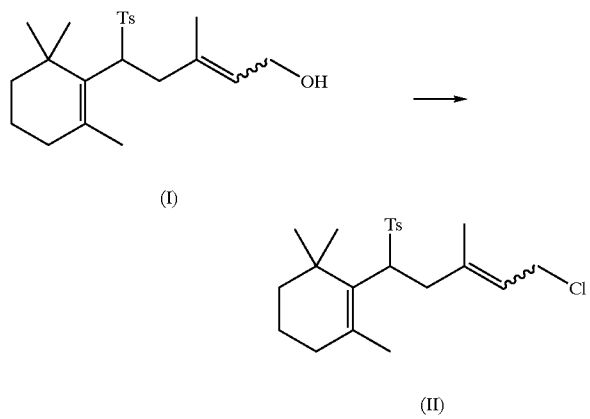

Alcohol (I) (trans/cis=96/4; 188 mg (0.5 mmole)) was dissolved in toluene (2.8 ml) at room temperature and acetone (395 mg (6.8 mmole)) was added dropwise thereto. Then, the mixture was cooled to 0° C. and 1 M TiCl$_4$ solution (1.2 ml) in toluene was added dropwise thereto at the same temperature. After addition, the mixture was stirred at the same temperature for 1 hour. After completion of the reaction, the reaction mixture was poured into water, followed by extraction with ethyl acetate. The resultant organic layer was washed in sequence with an aqueous saturated sodium bicarbonate solution and saturated saline and dried over anhydrous sodium sulfate, and the solvent was distilled off to obtain a yellow oily crude product. When the crude product thus obtained was quantified by HPLC, the yield of allyl halide (II) was 91% (trans/cis=91/9).

Example 4

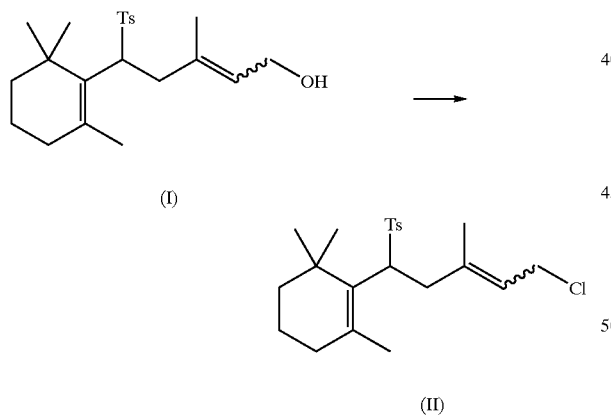

Phosphorus trichloride (137 mg (1.0 mmole)) was added dropwise to N,N-dimethylformamide (0.5 ml) at room temperature and the mixture was allowed to stand at the same temperature for 2.5 hours. Then, alcohol (I) (trans/cis=99/1; 377 mg (1.0 mmole)) was added thereto at the same temperature, followed by stirring for 1.5 hours. After completion of the reaction, the reaction mixture was poured into water and the mixture was extracted with ethyl acetate. The resultant organic layer was washed in sequence with an aqueous saturated sodium bicarbonate solution and saturated saline and dried over anhydrous sodium sulfate, and the solvent was distilled off to obtain a yellow oily crude product. When the crude product thus obtained was quantified by HPLC, the yield of allyl halide (II) was 99% (tans/cis=97/3).

Example 5

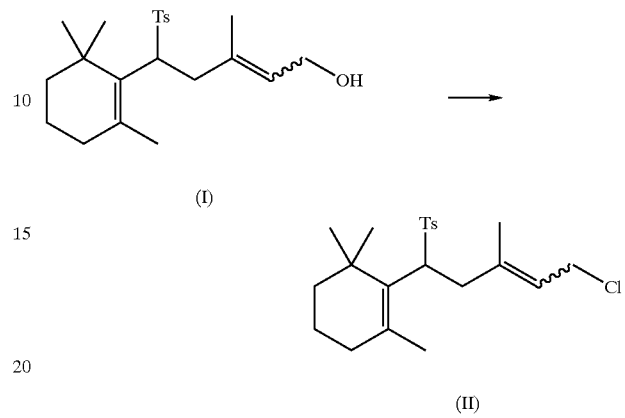

Alcohol (I) (trans/cis=99/1; 377 mg (1.0 mmole)) was added to a solution of phosphorus trichloride (137 mg (1.0 mmole)) in toluene (1.5 ml) at room temperature and the mixture was stirred for 3 hours. After completion of reaction, the reaction mixture was poured into water, followed by extraction with ethyl acetate. The resultant organic layer was washed in sequence with an aqueous saturated sodium bicarbonate solution and saturated saline and dried over anhydrous sodium sulfate, and the solvent was distilled off to obtain a yellow oily crude product. When the crude product thus obtained was quantified by HPLC, the yield of allyl halide (II) was 58% (tans/cis=92/8).

Example 6

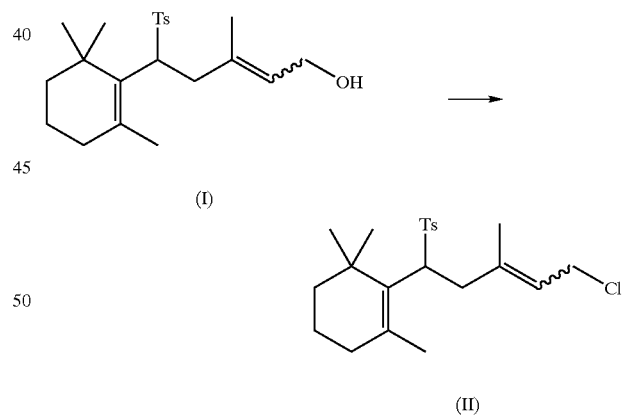

N,N-Dimethylformamide (36.5 mg (0.5 mmole) and phosphorus oxytrichloride (77 mg (0.5 mmole)) were added dropwise to toluene (1 ml) at room temperature and the mixture was allowed to stand at the same temperature for 1.5 hours. Then, a solution of alcohol (I) (trans/cis=99/1; 188 mg (0.5 mmole)) dissolved in toluene (0.5 ml) was added thereto at the same temperature and the mixture was stirred for 7.5 hours. After completion of the reaction, the reaction mixture was poured into water, followed by extraction with ethyl acetate. The resultant organic layer was washed in sequence with an aqueous saturated sodium bicarbonate solution and saturated saline and dried over anhydrous sodium sulfate, and the solvent was distilled off to obtain a yellow oily crude product. When the crude product thus obtained was quantified by HPLC, the yield of allyl halide (II) was 85% (tans/cis=97/3).

Example 7

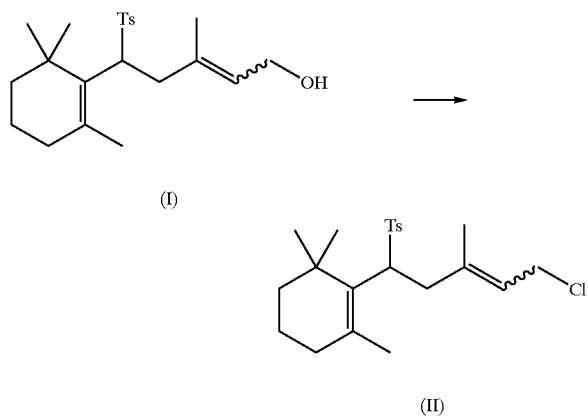

Phosphorus pentachloride (104 mg (0.5 mmole)) was added dropwise to N,N-dimethylformamide (0.5 ml) at room temperature and the mixture was allowed to stand at the same temperature for 1.5 hours. Then, alcohol (I) (trans/cis=99/1; 188 mg (0.5 mmole)) was added thereto at the same temperature and the mixture was stirred for 3 hours. After completion of the reaction, the reaction mixture was poured into water, followed by extraction with ethyl acetate. The resultant organic layer was washed in sequence with an aqueous saturated sodium bicarbonate solution and saturated saline and dried over anhydrous sodium sulfate, and the solvent was distilled off to obtain a yellow oily crude product. When the crude product thus obtained was quantified by HPLC, the yield of allyl halide (II) was 83% (tans/cis=98/2).

Example 8

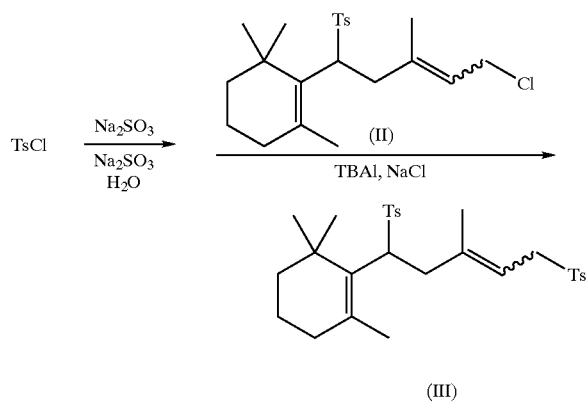

p-Toluenesulfonyl chloride (105 mg (0.55 mmole)), sodium sulfite (76 mg (0.60 mmole)), sodium carbonate (64 mg (0.60 mmole)) and $H_2O$ (3 ml) were charged into a reaction vessel at room temperature and, after raising the temperature to 50° C., the mixture was stirred for 2 hours. Then, tetra-n-butylammonium iodide (1.9 mg (0.005 mmole)) and sodium chloride (460 mg (200 wt %)) were added to the reaction mixture and further a solution of allyl halide (II) (90%; 230 mg (0.53 mmole)) dissolved in methyl isobutyl ketone (2 ml) was added dropwise thereto at the same temperature. The temperature of the mixture was raised to 88° C. and the mixture was stirred at the same temperature for 3 hours. After completion of the reaction, the reaction mixture was poured into an aqueous saturated ammonium chloride solution, followed by extraction with ethyl acetate. The resultant organic layer was washed in sequence with an aqueous saturated sodium bicarbonate solution and saturated saline and dried over anhydrous magnesium sulfate, and the solvent was distilled off to obtain a yellow oily crude product. When the crude product was quantified by HPLC, the yield of allyl sulfone (III) was 97%.

$^1$H-NMR(CDCl$_3$): δ 0.75 (3H* 70/100, s), 0.98 (3H*70/100, s), 0.78 (3H* 30/100, s), 1.00 (3H* 30/100, s), 1.15 (3H, s), 1.26–1.61 (7H, m), 1.98 (3H* 70/100, s), 2.00 (3H* 30/100, s), 2.44 (3H, S), 2.55 (3H, S), 2.57–3.06 (2H, m), 3.62–3.68 (1H, m), 3.82–3.87 (1H, t, J=8 Hz), 5.18–5.23 (1H, t, J=8 Hz), 7.26–7.35 (4H, m), 7.66–7.73 (4H, m).

Example 9

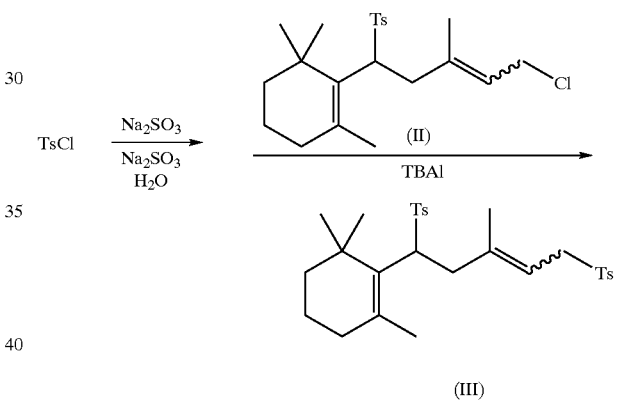

p-Toluenesulfonyl chloride (200 mg (1.05 mmole)), sodium sulfite (145 mg (1.15 mmole)), sodium carbonate (122 mg (1.15 mmole)) and $H_2O$. (1.5 ml) were charged into a reaction vessel at room temperature and, after elevating the temperature to 50° C., the mixture was stirred for 3 hours. Then, tetra-n-butylammonium iodide (3.69 mg (0.01 mmole)) was added to the reaction mixture and further a solution of allyl halide (II) (97.6% (trans/cis=94/6); 405 mg (1.0 mmole)) dissolved in toluene (1 ml) was added dropwise thereto at the same temperature. The temperature of the mixture was raised to 88° C. and the mixture was stirred at the same temperature for 5.5 hours. After completion of the reaction, the reaction mixture was poured into an aqueous saturated ammonium chloride solution, followed by extraction with ethyl acetate. The resultant organic layer was washed in sequence with an aqueous saturated sodium bicarbonate solution and saturated saline and dried over anhydrous magnesium sulfate, and the solvent was distilled off to obtain a yellow oily crude product. When the crude product was quantified by HPLC, the yield of allyl sulfone (III) was 93% (trans/cis=94/6).

Example 10

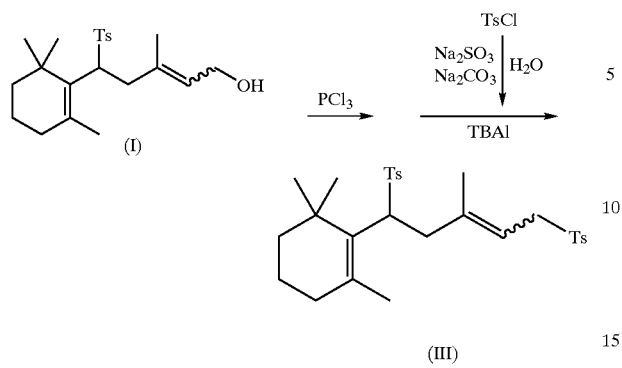

Phosphorus trichloride (137 mg (1.0 mmole)) was added dropwise to N,N-dimethylformamide (0.5 ml) at room temperature and the mixture was allowed to stand at the same temperature for 2.5 hours. Then, alcohol (I) (trans/cis=96/4; 377 mg (1.0 mmole)) was added thereto at the same temperature and the mixture was stirred for 1.5 hours. After completion of the reaction, the reaction mixture was poured into water, followed by extraction with ethyl acetate. The resultant organic layer was washed in sequence with an aqueous saturated sodium bicarbonate solution and saturated saline and dried over anhydrous sodium sulfate, and the solvent was distilled off to obtain allyl halide (II) (trans/cis=94/6) as a crude product.

Separately, p-toluenesulfonyl chloride (200 mg (1.05 mmole)), sodium sulfite (145 mg (1.15 mmole)), sodium carbonate (122 mg (1.15 mmole)) and $H_2O$ (1.5 ml) were charged into a reaction vessel and, after raising the temperature to 50° C., the mixture was stirred for 3 hours. Then, tetra n-butylammonium iodide (3.69 mg (0.01 mmole)) was added to the reaction mixture and further a solution of the above allyl halide (II) (trans/cis=94/6) dissolved in to toluene (1 ml) was added dropwise thereto at the same temperature. After raising the temperature to 88° C., the mixture was stirred at the same temperature for 5.5 hours. After completion of the reaction, the reaction mixture was poured into an aqueous saturated ammonium chloride solution, followed by extraction with ethyl acetate. The resultant organic layer was washed with saturated saline and dried over anhydrous sodium sulfate and dried over anhydrous sodium sulfate, and the solvent was distilled off to obtain a yellow oily crude product. When the crude product thus obtained was quantified by HPLC, the throughout yield of allyl sulfone derivative (III) from alcohol (I) was 92% (trans/cis=94/6).

Reference Example 1

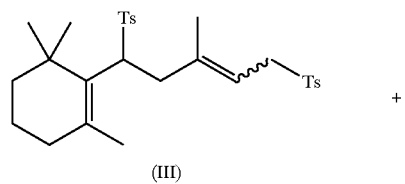

+

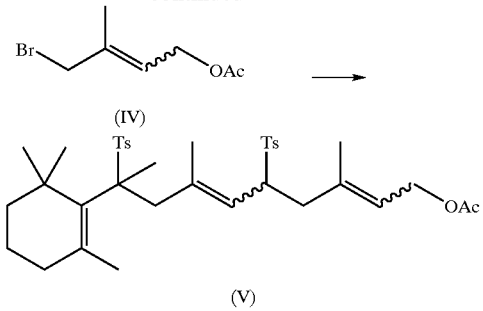

A solution of sodium hydride (60% suspension in oil; 19 mg (0.48 mmole)) dissolved in DMF (6 ml) was cooled to 0° C. and a solution of allyl sulfone derivative (III) (190 mg (0.37 mmole)) in DMF (3 ml) was added dropwise thereto within 20 seconds, followed by maintaining the mixture at the temperature for 20 minutes. Then, a solution of allyl halide (IV) (96%; 88 mg (0.41 mmole)) in DMF (3 ml) was added dropwise thereto at the same temperature within 5 minutes. The temperature was allowed to rise to room temperature and the mixture was stirred for 3 hours. After completion of the reaction, the reaction mixture was poured into an aqueous saturated ammonium chloride solution, followed by extraction with ethyl acetate. The resultant organic layer was washed in sequence with an aqueous saturated sodium bicarbonate solution and saturated saline and dried over anhydrous magnesium sulfate, and the solvent was distilled off to obtain a yellow oily crude product. When the crude product thus obtained was quantified by HPLC, the yield of disuflone derivative (V) was 94.8%.

Reference Example 2

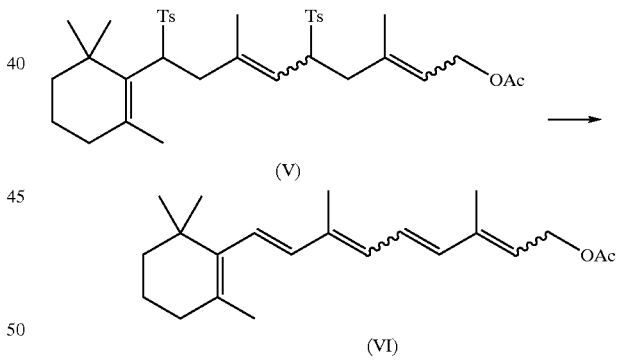

Disulfone derivative (V) (256 mg (0.4 mmole)) was dissolved in hexane (containing BHT (300 ppm); 2 ml), and 95% potassium hydroxide (240 mg (4 mmole)), methanol (7 mg (0.2 mmole)) and benzyltriethylammonium chloride (4 mg (0.02 mmole)) were charged thereinto, followed by stirring at 30° C. for 18 hours. After completion of the reaction, saturated saline was poured thereinto, and the mixture was extracted with ethyl acetate. The resultant organic layer was washed in sequence with water and saturated saline and dried over anhydrous sodium sulfate, and the solvent was distilled off to obtain red oily crude retinol. When the crude retinol thus obtained was acetylated according to a conventional manner and quantified by HPLC, the yield of retinol acetate (VI) was 91.3%.

Industrial Applicability

According to the present invention, an allyl sulfone derivative (3) can be produced from an allyl halide derivative (1) by using an inexpensive aryl sulfonyl chloride. This production process is an industrially advantageous process because the inexpensive starting material can be used, in addition, the desired product can be obtained in a high yield, even if water is present, and an expensive Pd catalyst, and a ligand are not required.

What is claimed is:

1. An allyl halide compound represented by the formula (1):

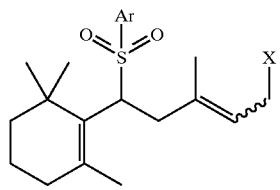
(1)

wherein Ar is an optionally substituted aryl group, X is a halogen atom, and the corrugated line means either one of E/Z geometrical isomers or a mixture thereof.

2. A process for producing an allyl sulfone compound represented by the formula (3):

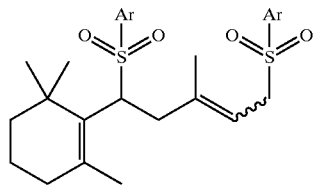
(3)

wherein Ar is an optionally substituted aryl group, and the corrugated line means either one of E/Z geometrical isomers or a mixture thereof, which comprises reacting an aryl sulfinic acid or a salt thereof represented by the formula (2):

  ArSO$_2$M (2)

wherein Ar is as defined above, and M is hydrogen atom, sodium atom or potassium atom, with an allyl halide compound represented by the formula (1):

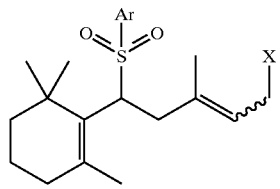
(1)

wherein x is a halogen atom, and Ar and the corrugated line are as defined above.

3. A process for producing an allyl sulfone compound represented by the formula (3):

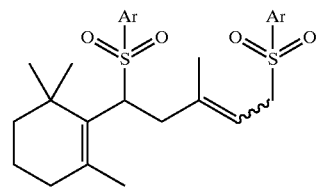
(3)

wherein Ar is an optionally substituted aryl group, and the corrugated line means either one of E/Z geometrical isomers or a mixture thereof, which comprises reducing an aryl sulfonyl chloride represented by the formula (4):

  ArSO$_2$Cl (4)

wherein Ar is as defined above to obtain an aryl sulfinic acid or a salt thereof represented by the formula (2):

  ArSO$_2$M (2)

wherein Ar is as defined above, and M is hydrogen atom, sodium atom or potassium atom, followed by, without isolation, reacting it with an allyl halide compound represented by the formula (1):

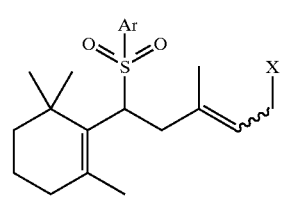
(1)

wherein X is a halogen atom, and Ar and the corrugated line are as defined above.

4. The process according to claim 3, wherein the allyl halide compound represented by the formula (1) is a compound obtained by subjecting an allyl alcohol compound represented by the formula (5):

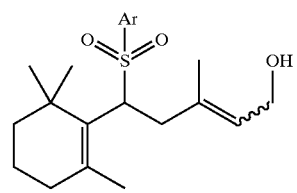
(5)

wherein Ar and the corrugated line are as defined in formula (1) to a halogenation reaction.

5. A process for producing the allyl halide compound represented by the formula (1) as defined in claim 1 which comprises reacting an allyl alcohol compound represented by the formula (5):

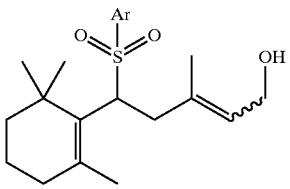

wherein Ar and the corrugated line are as defined in formula (1), with a halogenation agent.

6. The process according to claim 2, wherein the allyl halide compound represented by the formula (1) is a compound obtained by subjecting an allyl alcohol compound represented by the formula (5):

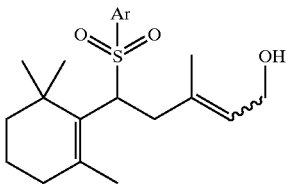

wherein Ar and the corrugated line are as defined in formula (1) to a halogenation reaction.

7. The process according to claim 5, 6 or 4 wherein the halogenation reaction is carried out by reacting a halogenation agent selected from a group consisting of a Group 4 halide a sulfur halide, phosphorus halide, boron halide, phosgene and oxalyl chloride.

8. The process according to claim 7, wherein the Group 4 halide is titanium tetrachloride.

9. The process according to claim 8, wherein the reaction is carried out in the presence of an ether compound or a ketone compound.

10. The process according to claim 9, wherein the reaction is carried out in the presence of a ketone compound.

11. The process according to claim 10, wherein the ketone compound is acetone.

12. The process for producing an allyl sulfone compound according to claim 7, wherein the sulfur or phosphorus halide is thionyl chloride, phosphorus trichloride, phosphorus pentachloride, or phosphorus oxychloride.

13. The process according to claim 5, 6 or 4 wherein the halogenation reaction is conducted by reacting a Vilsmeyer complex formed by reacting a sulfur halide, phosphorus halide, phosgene or oxalyl chloride with a formamide compound.

14. The process according to claim 13, wherein the formamide compound is N,N-dimethylformamide or N-methylformamide.

15. The process according to claim 3, 6 or 4, wherein the reduction reaction of an aryl sulfonyl compound represented by the formula (4) to an aryl sulfinic acid represented by the formula (2) or a salt thereof is carried out in water as a solvent in the presence of a reducing agent and a base.

16. The process according to claim 15, wherein the reducing agent is sodium sulfite, potassium sulfite, sodium bisulfite or potassium bisulfite.

17. The process according to claim 15, wherein the base is an alkali metal carbonate or an alkali metal bicarbonate.

18. The process according to claim 2, 3, 6 or 4, wherein an aryl sulfinic acid or a salt thereof is reacted with an allyl halide compound represented by the formula (1) in the presence of a phase-transfer catalyst in a biphasic system consisting of water and a hydrophobic organic solvent.

19. The process according to claim 18, wherein the phase-transfer catalyst is a quaternary ammonium salt.

20. The process according to claim 19, wherein the quaternary ammonium salt is quaternary ammonium iodide.

21. The process according to claim 2, 3, 6 or 4, wherein an inorganic salt is added to the reaction of the allyl sulfinic acid or a salt thereof with the ally halide compound represented by the formula (1).

22. The process according to claim 21, wherein the inorganic salt is an alkali metal or alkaline earth metal halide.

23. The process according to claim 22, wherein the alkali metal halide is sodium chloride.

* * * * *